US005517989A

United States Patent [19]
Frisbie et al.

[11] Patent Number: 5,517,989
[45] Date of Patent: May 21, 1996

[54] GUIDEWIRE ASSEMBLY

[75] Inventors: Jeffrey S. Frisbie, San Jose; Paul D. Corl, Palo Alto; John E. Ortiz, East Palo Alto, all of Calif.

[73] Assignee: Cardiometrics, Inc., Mt. View, Calif.

[21] Appl. No.: 222,137

[22] Filed: Apr. 1, 1994

[51] Int. Cl.$^6$ .......................... A61B 5/0408; A61B 8/06; A61N 1/05

[52] U.S. Cl. ............... 128/642; 128/661.08; 128/662.06; 128/692; 607/122; 606/41

[58] Field of Search ........................... 128/642, 639, 128/661.08, 661.09, 662.06, 692, 702; 607/122; 606/41

[56]  References Cited

U.S. PATENT DOCUMENTS

| | | |
|---|---|---|
| 4,481,953 | 11/1984 | Gold et al. |
| 4,660,571 | 4/1987 | Hess et al. |
| 4,771,788 | 9/1988 | Millar. |
| 4,841,981 | 6/1989 | Tanabe et al. ............... 128/642 |
| 4,920,967 | 5/1990 | Cottonaro et al. |
| 4,936,281 | 6/1990 | Stasz. |
| 4,957,110 | 9/1990 | Vogel et al. |
| 4,961,433 | 10/1990 | Christian. |
| 4,967,753 | 11/1990 | Haase et al. |
| 4,991,588 | 2/1991 | Pflueger et al. |
| 5,059,851 | 10/1991 | Corl et al. |
| 5,098,431 | 3/1992 | Rydell. |
| 5,104,393 | 4/1992 | Isner et al. |
| 5,105,818 | 4/1992 | Christian et al. |
| 5,125,137 | 6/1992 | Corl et al. |
| 5,156,151 | 10/1992 | Imran. |
| 5,163,445 | 11/1992 | Christian et al. |
| 5,174,295 | 12/1992 | Christian et al. |
| 5,174,299 | 12/1992 | Nelson ........................... 128/642 |
| 5,178,159 | 1/1993 | Christian. |
| 5,184,621 | 2/1993 | Vogel et al. |
| 5,246,438 | 9/1993 | Langberg ........................ 128/642 |
| 5,257,451 | 11/1993 | Edwards et al. |
| 5,279,299 | 1/1994 | Imian ............................. 128/642 |
| 5,318,525 | 6/1994 | West et al. ........................ 607/122 |
| 5,327,905 | 7/1994 | Avitoll ............................. 607/122 |

FOREIGN PATENT DOCUMENTS

| | | |
|---|---|---|
| WO94/16632 | 8/1994 | WIPO. |
| WO94/16618 | 8/1994 | WIPO. |
| WO94/16619 | 8/1994 | WIPO. |

OTHER PUBLICATIONS

Cardiometrics, Flo Wire/Flo Map Jun., 1992.
Diagnosis of Intermediate Lesion FloWire Doppler Guide Wire Case Study–Cardiometrics–Nov. 1992 by Morton J. Kern, M.D.
Cardiometrics–Assessment of Secondary Lesion Severity FloWire Doppler Guide Wire Case Study–Oct. 1991 by Jerome Segal, M.D.
Cardiometrics–Clinical Value of Coronary Blood Flow Velocity Feb. 1993.
Validation of a Doppler Guide Wire for Intravascular Measurement of Coronary Artery Flow Velocity–"circulation" vol. 85, No. 5 May 1992 by Joseph W. Doucette, M.D. et al.

(List continued on next page.)

Primary Examiner—Lee S. Cohen
Attorney, Agent, or Firm—Oblon, Spivak, McClelland, Maier & Neustadt

[57]  ABSTRACT

A method of diagnosing and treating the human or animal body comprises feeding a flexible guide wire, dimensioned to be inserted into human coronary arteries, along a blood vessel in the human or animal body and epicardially mapping the electrocardiographic signals by means of electrodes secured to the guide wire. The method of diagnosing and treating the human or animal body may include the step of ablating selected body tissue by establishing a DC or radio frequency current through the body tissue between a pair of electrodes in which at least one of the electrodes is located on the guide wire. The method may also include passing flowable material to or from selected tissue by means of a catheter passed over the guide wire. The method may optionally include sensing the velocity of blood flow in the blood vessel by means of a velocity sensor mounted on the guide wire, or the temperature of selected body tissue by means of a temperature sensor mounted on the guide wire.

23 Claims, 5 Drawing Sheets

OTHER PUBLICATIONS

Analysis of Coronary Blood Flow Velocity Dynamics in Angiographically Normal and Stenosed Arteries Before and After Endolumen Enlargement by Angioplasty–vol. 21, No. 2–Feb. 1993 by Elizabeth O. Ofili, M.D., MPH, et al.

Atlas of Ischemic Heart Disease by E. William Hancock, M.D., Edwin Alderman, M.D., and Michael Stadius, M.D., Editors–1989.

Alterations of Phasic Coronary Artery Flow Velocity in Humans During Percutaneous Coronary Angioplasty–vol. 20, No. 2, Aug. 1992 by Jerome Segal, M.D., FACC, et al.

Determination of the Hemodynamic Significance of Angiographically Intermediate Coronary Stenoses by Intracoronary Doppler Flow Velocity vol. 19, No. 3–Mar. 1, 1992 by Thomas J. Donohue, et al.

Restoration of Flow in a Peripheral Vessel FloWire Doppler Guide Wire Case Study by Jeffrey M. Isner, M.D.–Nov. 1992.

Diagnosis of Intermediate Lesion FloWire Doppler Guide Wire Case Study–Oct. 1991 by Morton J. Kern, M.D.

Return of Diastolic Predominant Flow Post–PTCA FloWire Doppler Guide Wire Case Study–Oct. 91.

Cardio Intervention–The Journal of News and Reviews in Invasive Cardiology–vol. 3, No. 1–Mar. 1993.

The American Journal of Cardiology–A Symposium: The Clinical Applications of the Intracoronary Doppler Guidewire Flow Velocity in Patients: Understanding Blood Flow Beyond the Coronary Stenosis. May 20, 1993 by Morton J. Kern, M.D. and H. Vernon Anderson, M.D.

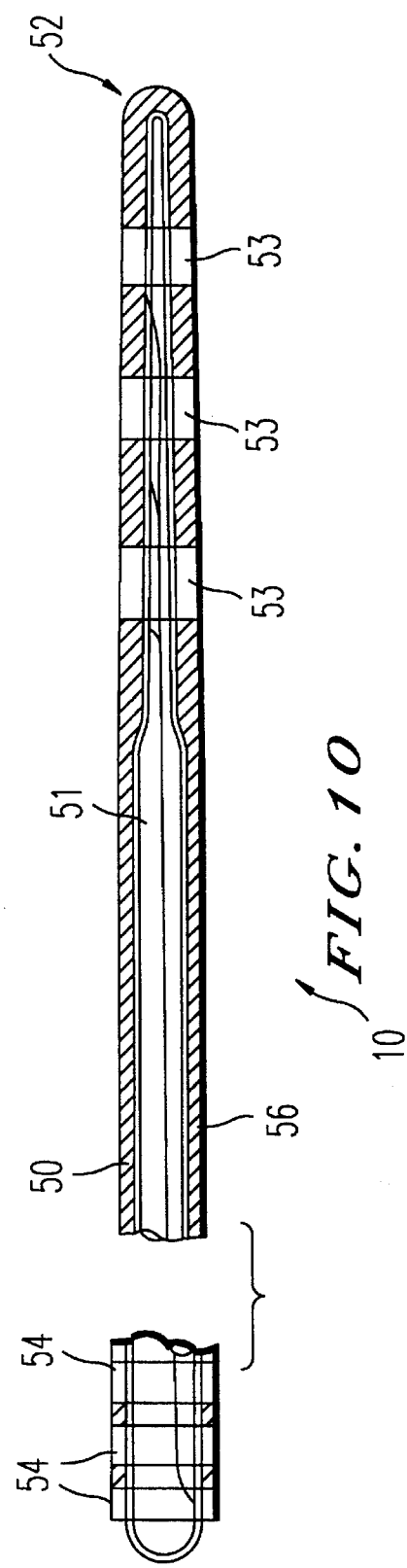
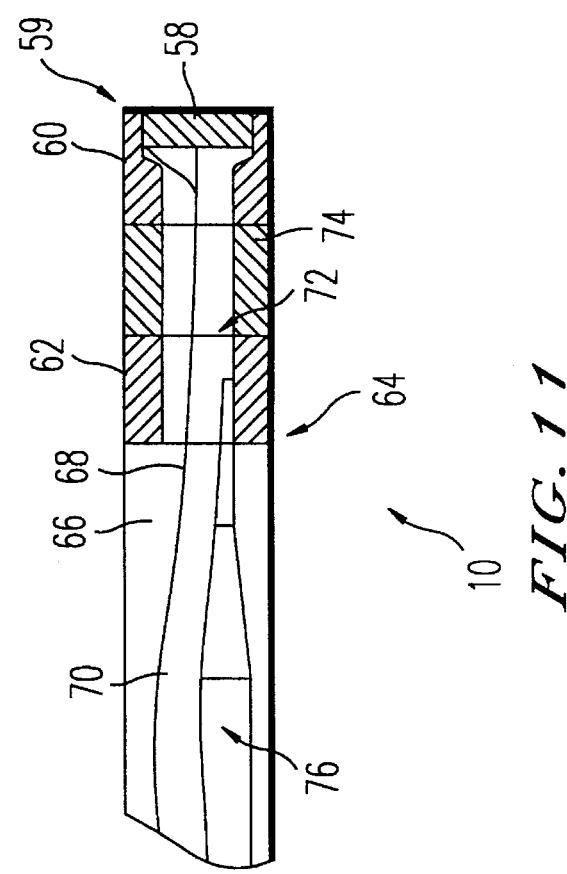

GUIDEWIRE ASSEMBLY

FIELD OF THE INVENTION

This invention relates to a method and an apparatus for diagnosis of medical conditions of the human or animal body. In particular it relates to a method and an apparatus for mapping electrical activity in, for example, the heart or brain to locate arrhythmias for subsequent treatment by means of ablation. It relates specifically to an epicardial approach to achieve this purpose.

BACKGROUND OF THE INVENTION

An abnormal condition of the heart's electrical conduction system can exist that causes irregular heartbeats. There are various forms of these abnormalities that can cause the irregular heartbeats, or arrhythmias, including coronary artery disease, cardiomyopathy, congenital and valvular heart disease, metabolic disorders, and drug toxicity. Arrhythmias are even known to develop in structurally normal hearts. Whichever the cause and manifestation of the arrhythmia, the irregular heartbeat results in disruption of the smooth contraction sequence of the heart muscle and compromises the heart's ability to pump blood out to the rest of the body.

It is thus important that a process should exist allowing the source of such arrhythmias to be located. Electrocardiographic mapping allows this to be achieved. In the past, electrocardiographic mapping, however, typically required open heart surgery in which a grid of electrodes was wrapped around the heart on the epicardial surface. In order to avoid open heart surgery and to allow the mapping to be performed percutaneously, endocardial mapping processes have been developed. These involve the insertion of a catheter into the heart chambers in order to probe the endocardial surfaces to locate the general area from which an arrhythmia emanates. Should intervention be desired in order to stop the arrhythmia, the precise location of its source must be known. While an endocardial approach allows the general location of the source of an arrhythmia to be determined, the epicardial approach will provide more accurate results. In particular it is desirable to be able to map the electrocardiographic patterns using a percutaneous technique. The present invention accordingly provides a means to achieve this by mapping the coronary arteries lying on the epicardial surface of the heart.

OBJECTS AND SUMMARY OF THE INVENTION

It is an object of the invention to provide a method and an apparatus for mapping the electrical activity of the heart/brain.

It is a further object of the invention to treat heart disease by means of a guide wire.

Yet another object of the invention is to monitor the flow velocity of blood without invasive surgery and to combine this with a blood or tissue mapping or coagulation device inserted through the skin, also referred to as percutaneous treatment.

A further object of the invention is to provide a percutaneous tissue or blood coagulation device with a temperature sensing capability.

According to the invention there is provided a method of diagnosing medical conditions of the human or animal body, which comprises feeding a guide wire along at least one blood vessel in the human or animal body, and sensing electrical activity in the body by means of at least one electrode secured to the guide wire.

The method can include sensing the electrical activity at various locations along the length of at least the one blood vessel.

The method can include detecting abnormal electrical activity in the form of an arrhythmia by inducing the arrhythmia. The arrhythmia may be induced by applying electrical pulses via an endocardial pacing lead.

The method typically includes comparing the sensed signals to determine the location at which a signal is first detected.

A stationary electrode, which is stationary relative to the body, can be used as a reference electrode.

Further according to the invention there is provided a method of treating an arrhythmia in a human or animal body, which comprises feeding a guide wire along at least one blood vessel in the human or animal body, and sensing the electrical activity in the body by means of at least one electrode secured to the guide wire, to locate the arrhythmia, and establishing a current through selected body tissue between a pair of electrodes, at least one of the electrodes being located on the guide wire thereby to ablate at least a part of the selected body tissue.

The current emitted from or received by an electrode on the guide wire may be direct current or a radio frequency signal produced by an external power source.

The method can include sliding a catheter tube over the guide wire and passing fluid to or from selected body tissue.

The method can further include sensing, by means of a velocity sensing means mounted on the guide wire, the velocity of blood flow in the blood vessel in which the sensing means is located, or sensing the temperature of selected body tissue by means of a temperature sensing means mounted on the guide wire.

Still further, according to the invention there is provided a guide wire assembly, which comprises a flexible guide wire having lateral dimensions in the range of from 0.010" to 0.038", and at least one electrode secured to the guide wire.

The electrode can be a unipolar electrode.

The guide wire assembly can include a velocity sensing means for sensing the blood flow velocity in a blood vessel, wherein the velocity sensing means can include a Doppler ultrasound transducer.

The assembly can also include a temperature sensing means for sensing the temperature of selected body tissue in the human or animal body.

The assembly can further include a catheter tube means, passable over the guide wire, for passing fluid to or from selected body tissue.

Still further according to the invention, there is provided an elongate guide wire having a proximal and a distal end, at least a portion of the wire near the distal end being flexible, which includes a central core; a tubular body, at least partially surrounding the central core; and at least one electrode secured relative to the body, wherein the central core extends along at least part of the length of the guide wire, and wherein the guide wire has lateral dimensions in the range of from 0.010" to 0.038".

The body can include an electrically conductive or non-conductive smooth proximal sleeve section.

The body can include distal helical spring sections.

The electrode can include a cylindrical, electrically non-conductive tubular support with helical portions extending axially from both ends of the support for securing the support to the body.

The support can be formed in two parts which are axially connectable to each other by means of complementary locking formations formed at opposed ends of the two parts.

The helical portions can comprise helical grooves in an outer surface of the support.

The electrode can include a conductive layer formed on part of an outer surface of the support.

The conductive layer can comprise a conductive tube which is split longitudinally.

The conductive layer can comprise a conductive ribbon wound on the support.

The electrode can include a central, electrically conductive cylinder and electrically non-conductive helical portions extending axially from both ends of the cylinder.

The lateral dimensions of the core can decrease towards its distal end.

The decrease in the lateral dimensions of the core can comprise a plurality of discrete steps.

The decrease in the lateral dimensions of the core can comprise a continuous gradual taper.

The guide wire can include a plurality of electrodes, each associated with a conductor extending centrally along a central cavity defined by the body.

The guide wire can include a non-conductive outer layer covering the intervening portions between the electrodes, thereby to provide the guide wire with a smooth outer surface.

Still further according to the invention there is provided a method of making a guide wire which comprises providing an elongate core having decreased lateral dimensions towards its distal end; at least partially surrounding the core with a tubular body to provide a structure having increased flexibility towards a distal end thereof; and attaching an electrode on the body.

The method may include depositing a non-conductive polymer on the body, leaving the electrode exposed, to a thickness corresponding to the extent to which the electrode extends radially from an outer surface of the body so that the guide wire has a smooth outer surface.

The electrode can include a conductive cylinder which is formed on an electrically non-conductive support by insert molding, the electrode being secured to the body by means of connecting means formed on the support.

The electrode can be an electrically conductive cylinder which is split longitudinally, the cylinder being secured to an electrically non-conductive support and connected to the body by means of the connecting means on the support.

The body can be formed as a plurality of sections, the method including connecting the sections to each other along a common longitudinal axis.

The method can include forming the electrode by sputtering a metal coating onto an outer surface of an electrically non-conductive tubular support, and connecting the support between two sections of the body.

The method can include forming the electrode by wrapping a conductive ribbon around an electrically non-conductive tubular support and connecting the support between two sections of the body.

BRIEF DESCRIPTION OF THE DRAWINGS

FIG. 10 is a sectional side view of another embodiment of a guide wire in accordance with the invention;

FIG. 11 is a sectional side view of another embodiment of the guide wire in accordance with the invention, showing the distal portion thereof.

DETAILED DESCRIPTION OF THE INVENTION

An electrocardiographic mapping device is described in U.S. patent Ser. No. 5,156,151, the entire contents of which are incorporated herein, by reference.

Figure 1:
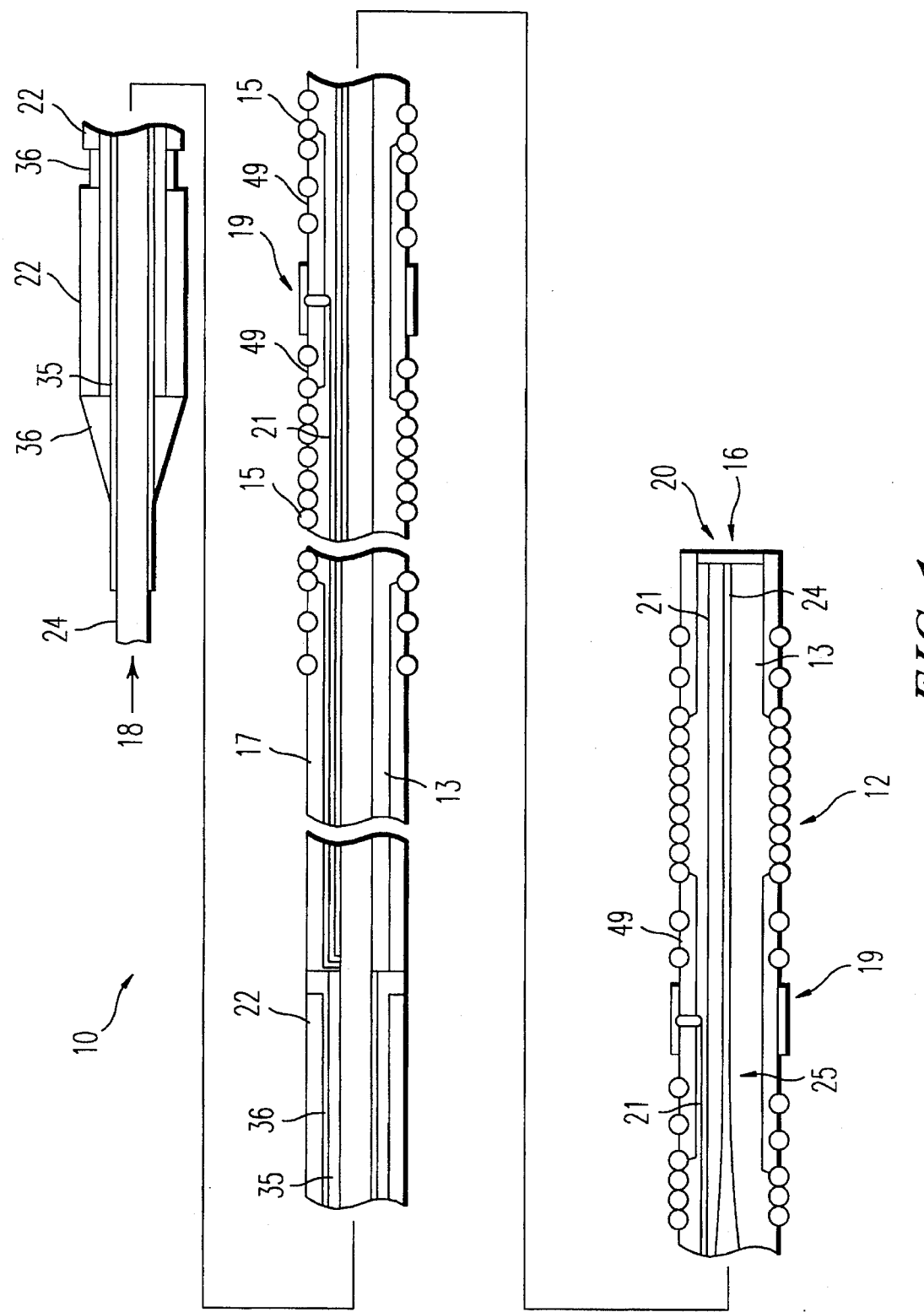
FIG. 1 is a sectional side view of a guide wire in accordance with the invention.

Referring to FIG. 1, a guide wire in accordance with the invention is indicated generally by reference numeral 10, and includes an elongate tubular body 12 defining a central elongate cavity 13. The body 12 is made of an electrically conductive material which comprises spring coils 15 towards the distal end 16 of the body 12, and a smooth sleeve section 17 towards the proximal end 18. The body 12 can equally well be constructed from an electrically non-conductive material. The proximal end 18 is connected to a rotary connector (not shown). Two spaced, sleeve-like electrodes 19 surround the body 12 near its distal end 16 and an end electrode 20 is located on the distal end 16. These are connected electrically, by means of electrical conductors 21 extending longitudinally along the cavity 13 to electrical contacts 22 mounted at the proximal end of the tubular body 12.

A core 24 extends along the length of the body 12 and provides the guide wire 10 with a certain amount of rigidity. The core 24 is tapered towards the distal end 16 to give the wire 10 greater flexibility towards the distal end 16. In the embodiment illustrated in FIG. 1, the tapering takes place in successive gradual steps, one of which is illustrated in FIG. 1 in the portion depicted by reference numeral 25. In this particular embodiment the tapering steps commence at locations approximately 15 to 20 centimeters from the distal end 16 (not shown), and 2 to 3 centimeters from the distal end 16 (depicted by numeral 25), respectively. Furthermore the core 24 is flattened from a point about 1 to 1.5 centimeters from the distal end 16 to define an oval cross section. The spring coil 15 is also stretched somewhat at its distal end (not shown) to provide the wire 10 with greater flexibility at the distal end 16.

Figure 2:
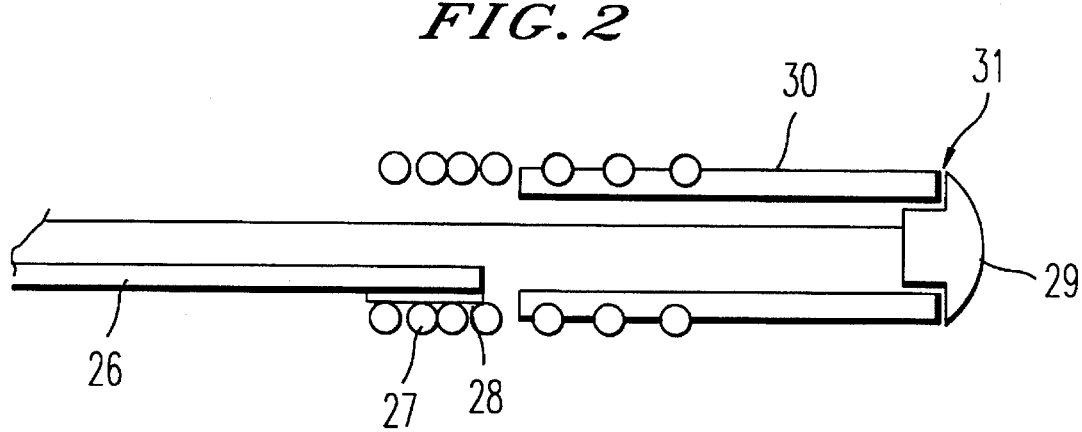
FIG. 2 is a sectional side view of the distal portion of another embodiment of the wire.
Figure 3:
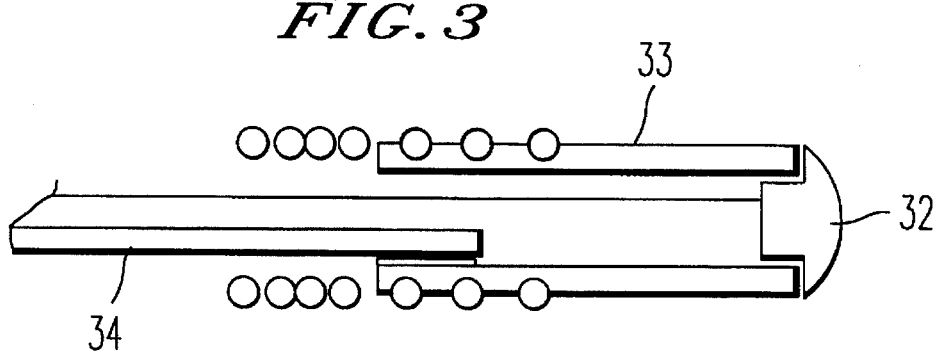
FIG. 3 is a sectional side view of the distal portion of yet another embodiment of the wire.
Figure 4:
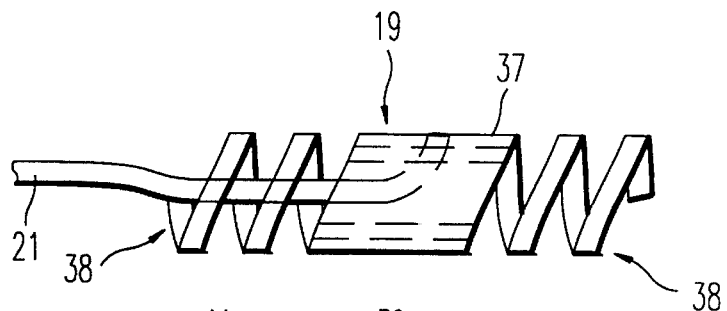
FIG. 4 is a side view of one embodiment of an electrode arrangement in accordance with the invention.

In the embodiment illustrated in FIG. 2 the core 26 is secured at its distal end to the most distally located spring coil 27 by means of a solder joint 28 as shown in FIG. 2. In this embodiment, the electrode 29 is electrically insulated from the spring coil 27 by means of a nonconductive support sleeve 30. The electrode 29 in this embodiment is a cap-like electrode with a convex distal face, which has been found to work particularly well. The sleeve 30 is adhesively secured to the electrode 29, for example by means of an epoxy or a cyanoacrylate adhesive (not shown) at the joint 31. In another embodiment, illustrated in FIG. 3, the electrode 32 is attached to a conductive support sleeve 33 by means of an adhesive (not shown). The electrode 32 and sleeve 33 are electrically insulated from each other by means of the adhesive which could be any suitable non-conductive adhesive, for example an epoxy or cyanoacrylate. Instead a separate insulator can be secured between the electrode 32 and the sleeve 33. The core 34 is soldered directly to the sleeve 33 in this case. In all the embodiments the core serves to provide the wire 10 with stability by holding the sections of the body 12 together.

Referring again to FIG. 1, the spring coils 15 making up the distal part of the body 12 are formed in sections intermediate the electrodes 19, the coils near the distal end being made of a radiopaque material, e.g. any of various alloys of platinum, palladium or gold, to make the distal end more easily visible under X-rays, while the more proximal coils are made of stainless steel. The core 24 is made of stainless steel or nickel titanium.

The contacts 22 are electrically insulated from the core 24 by means of a sheath 35 of a thin-walled material such as polyimide intermediate the contact 22 and the core 24. The contacts 22 are secured to the sheath 35 by means of an adhesive 36, for example an epoxy, a moisture cure or a light cure (typically ultra violet light). The adhesive 36 also serves to smoothen the transition between the contacts 22 and the body 12. The electrical conductors 21 are secured to the contacts 22 and electrodes 19, 20 by means of a soldering process.

Various embodiments of the electrodes 19 are depicted in FIGS. 4 to 8. All the electrodes 19 shown comprise a central cylindrical portion and spiral end portions. In the embodiment illustrated in FIG. 4, the central cylindrical portion 37 is made of a conductive material which is joined e.g. by means of an adhesive, to the two end portions 38 which are made of an electrically non-conductive material. In this embodiment the central portion 37 is soldered to an electrical conductor 21.

Figure 5:
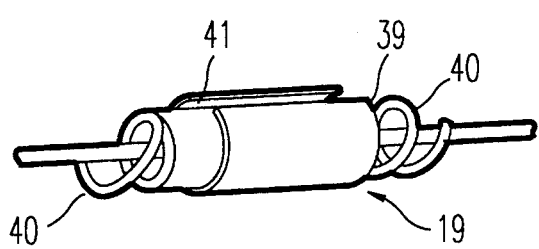
FIG. 5 is a three-dimensional view of another embodiment of an electrode arrangement.

In the embodiment illustrated in FIG. 5 the central portion 39 is formed integrally with the portions 40. In this embodiment both the central portion 39 and the end portions 40 are made of an insulating material e.g. a polymer or ceramic material. If a polymer is used, a semirigid variety, for example a glass-filled variety, is preferable. The electrode 19 includes a split sleeve 41 which is slipped over the central portion 39. The sleeve 41 is then secured in place by means of adhesive or a crimping process.

Figure 6:
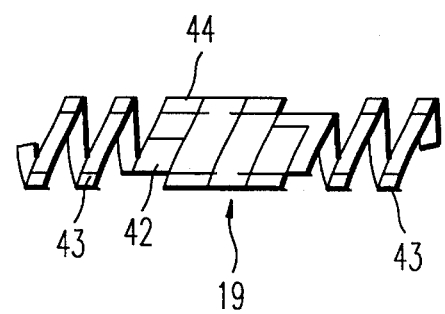
FIG. 6 is a side view of yet another embodiment of an electrode arrangement.

In the embodiment illustrated in FIG. 6 the central portion 42 and end portions 43 are similar to those illustrated in FIG. 5. The electrode 19, in this embodiment, takes the form of a conductive ribbon 44 which is wrapped around the central portion 42, which acts as a support for the ribbon 44. The ribbon 44 is secured by means of conventional means, e.g. an adhesive.

Instead of wrapping a ribbon 44 around the portion 42 in the FIG. 6 embodiment electrode 19 may be formed by sputtering a metal onto the portion 42 and, either masking off, during the sputtering process, areas not to be coated, or subsequently removing the metal from the portions that are not to be coated, e.g. by an etching process.

Figure 7:
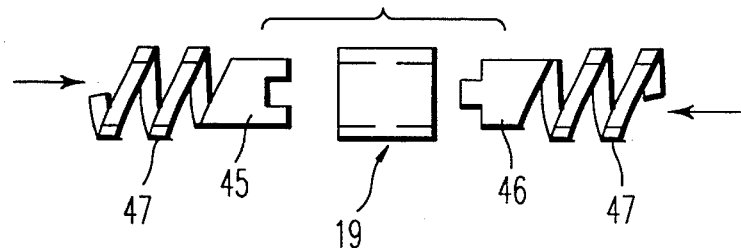
FIG. 7 is a side view of yet another embodiment of an electrode arrangement.
Figure 8:
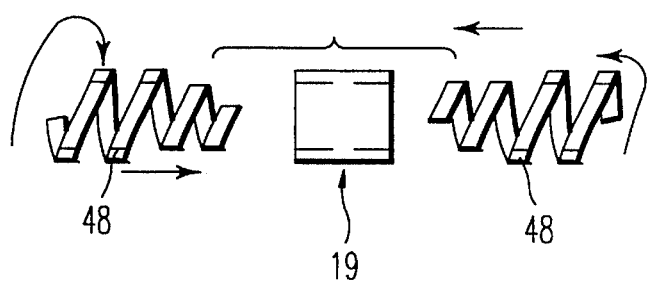
FIG. 8 is a side view of yet another embodiment of an electrode arrangement.

Instead of the central portion being formed as a unitary structure, it may be formed in two sections, as illustrated in FIGS. 7 and 8. In FIG. 7 the two sections 45, 46 of the central portion have complimentary, opposed, keyed ends for matingly securing the two portions 45, 46 to one another. The end portions 47 extend outwardly from the two sections 45, 46. In FIG. 8 no actual cylindrical portion is defined. Instead, the spiral portions 48 engage one another in an interlocking thread arrangement to define a central support when engaged (not shown).

In each case the outwardly facing spiral portions are engageable with the spring coils of the body 12 in an interlocking thread manner.

Figure 9:
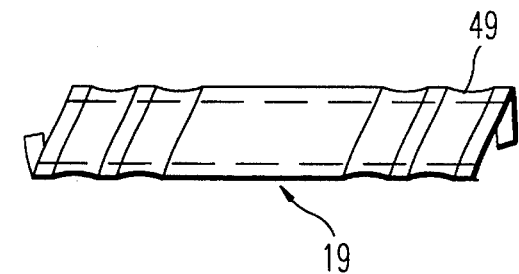
FIG. 9 is a side view of another embodiment of an electrode arrangement.

It will be appreciated that the thread portions may, instead, take the form of spirally grooved sections 49 as illustrated in FIG. 9. This embodiment is also shown in FIG. 1.

Referring again to FIG. 1, more than one electrode 19 may be provided, the embodiment in FIG. 1 having two radially extending electrodes 19 and distal electrode 20. The electrode 20 is received in plug-like fashion in the distal end 16 of the body 12. A separate conductor 21 is associated with each electrode 19 and 20 and, as mentioned above, interconnects its electrode with a corresponding electrical contact 22. The electrical conductors 21 are secured to the electrodes 19, 20 and the contacts 22 by conventional means, e.g. by a soldering process. The contacts 22 are sleeve-like formations that are aligned substantially coaxially with the tubular body 12.

In the embodiments described thus far, the basic structure of the tubular body 12 includes helical springs 15. A similar flexible guide wire 10 can be provided by dispensing with the spring coils 15 and, instead, making use of a polymer sheath 50 surrounding the core 51, as illustrated in FIG. 10. The diameter of the core 51 gradually decreases as illustrated in FIG. 10 or may be stepped, both options achieving the same result of providing a structure having increased flexibility towards its distal end 52. Sleeve-like electrodes 53 and contacts 54 are thereafter secured at predetermined intervals along this sheath 50, whereafter a second outer polymer coating 56 is provided intermediate the electrodes 53 so as to further secure the electrodes 53 and the contacts 54, and to provide the guide wire 10 with a smooth outer surface. The polymer sheath 50 and coating 56 could be made of flexible compound such as polyurethane. Clearly this embodiment could be provided with a distal electrode as shown in the FIGS. 1, 2, and 3 embodiments.

Instead of merely serving as a means for mapping and ablating by virtue of the electrodes, the wire 10 may further include sensors for measuring blood flow velocity in the blood vessel and/or the temperature of blood or tissue. Referring, for instance, to FIG. 11, a guide wire 10 having a sensor 58 attached to its distal end 59, is illustrated. The sensor 58 may be a Doppler ultrasound transducer for measuring the blood flow velocity in a blood vessel or may be any other desired sensor, e.g. for measuring the temperature of tissue. In the illustrated embodiment the sensor 58 is mounted on its own housing 60.

An electrode 62 is secured to the distal end 64 of the most distal spring coil 66 intermediate the coil 66 and the sensor housing 60. Conductors 68, connecting the sensor 58 to associated circuitry located externally to the wire 10, extend into the central cavity 70 and pass through a central opening 72 in the electrode 62. The sensor 58 is thus connected electrically to electrical circuitry (not shown), at the proximal end of the body by means of the electrical conductor 68. If the housing 60 is made from an electrically conductive material, the housing 60 is electrically insulated from the electrode 62 by means of a cylindrical insulator 74 intermediate the electrode 62 and the housing 60. In this embodiment, the core 76 serves as a conductor connecting the electrode 62 with a contact (not shown). In order electrically to insulate the core 76 from the conductors 68, the core 76 is provided with an insulating coating (not shown). It will be appreciated that, instead of using the core 76 as a conductor, the electrode 62 could be connected to its contact by means of a separate conductor similar to the conductors 68.

The guide wire 10 has numerous applications. It can, for instance, be used to map electrical activity from any suitable blood vessel e.g. in the heart or the brain. For convenience, the description below refers specifically to the use of the wire 10 in coronary arteries.

The guide wire 10 may be manipulated along a suitable blood vessel into a desired coronary artery to perform functions epicardially. The electrodes allow epicardial mapping to be performed by monitoring the electrocardial patterns, as is described in greater detail below. Thereby arrhythmias can be located. In addition, a sensor attached to the guide wire 10 may be used to measure blood flow velocity, temperature or any other variable of interest depending on the nature of the sensor. The electrodes perform the further function of ablation by connecting a direct current or radio frequency voltage source to the electrical contacts 22. One or more suitable electrodes may be placed externally to the electrodes on the wire 10 for selective coagulation of body tissue. Instead, a potential difference may be established across any two electrodes on the wire 10 to cause ablation of tissue intermediate these two electrodes.

If a patient presents with an irregular heartbeat, the region from which it originates can be determined generally using electrocardiograms. However, if intervention is desired in order to stop the arrhythmia, the precise location must be known. As mentioned above, current methods for determining the location include percutaneously inserting an electrode catheter into one of the heart chambers and positioning it at various locations on the chamber's endocardial surface to locate the general location of an arrhythmia. Another, more accurate, method requires open heart surgery in which the chest is opened and the heart exposed. Electrodes are then placed at various points on the epicardial surface. With the present invention, a very precise epicardial approach can be accomplished percutaneously, rather than opening the chest, by inserting the guide wire 10 of the present invention into the coronary arteries, which lie on the epicardial surface of the heart.

Figure 12:
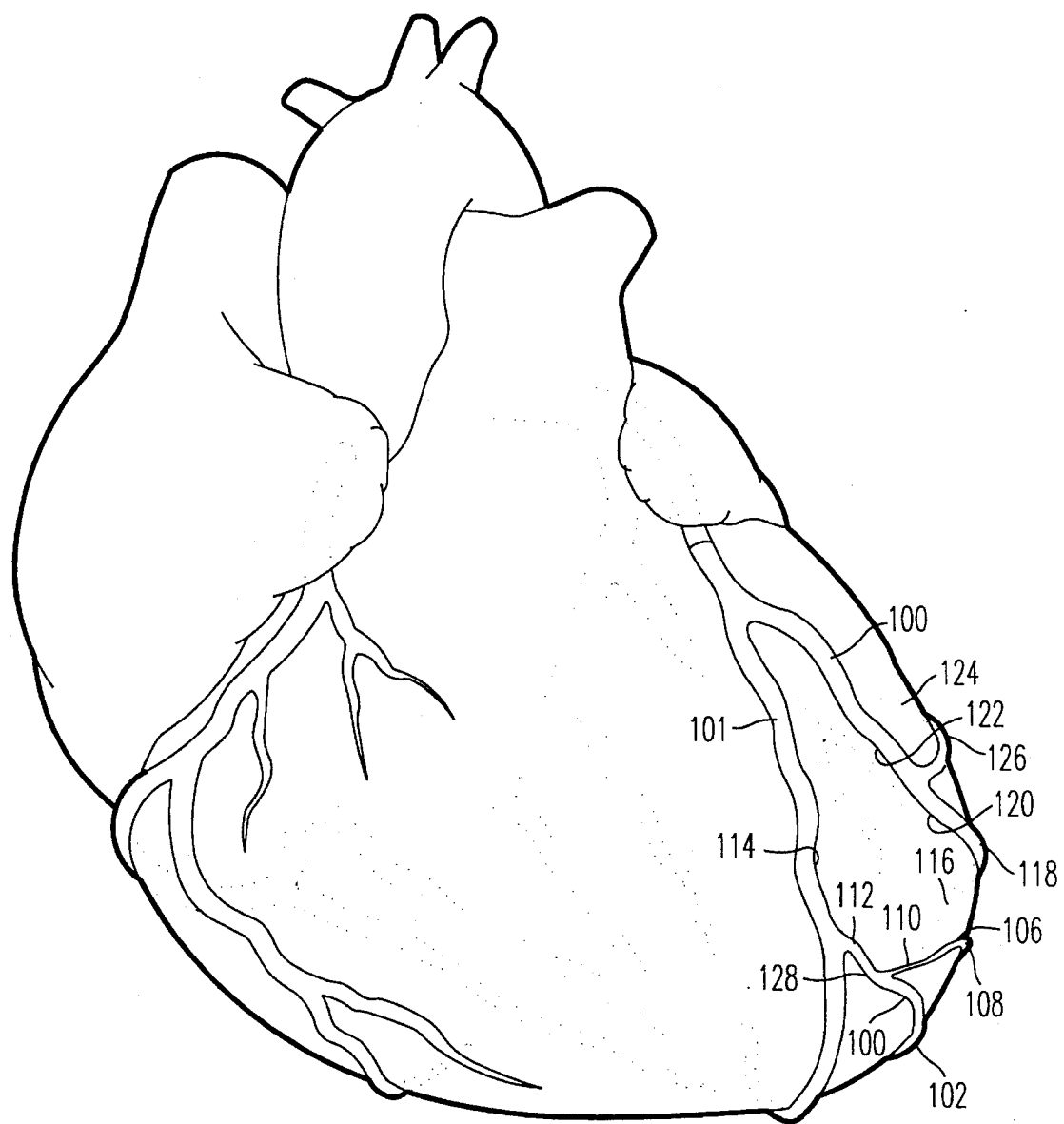
FIG. 12 is a three-dimensional view of a human heart.

Referring to FIG. 12, the guide wire 10 is used to generate an electrical map of the arterial system of the heart to precisely locate the origin of an arrhythmia, the approximate location of which may have been previously determined through the use of electrodes on the body surface. The guide wire 10 is steered into any of the coronary arteries or their branches. Access to the arteries is percutaneous using standard techniques either from the femoral or brachial artery. Each unipolar electrode on the wire is capable of sensing the local electrical activity of the heart muscle. The activity at various points along the length of an artery, and possibly in several arteries, is sampled as discussed in greater detail below. The origin of the arrhythmia is then localized by comparing the sampled signals and determining the earliest occurrence. Any stationary electrode, such as a surface electrode, is used as a reference signal. With multiple electrodes on the wire, multiple sites can be sampled simultaneously. The device thus needs to be repositioned fewer times, and the mapping procedure may be accomplished more quickly.

In practice intravascular mapping would involve first locating the general site of the arrhythmia. In this case the electrocardiographic assessment reveals the arrhythmia to be in the tissue served by the left anterior first diagonal artery 100 and left anterior descending artery 101. Now the specific branch needs to be determined. For the purposes of this example, a guide-wire 10 having two unipolar electrodes 19 is used.

The wire 10 is initially positioned with its distal end 16 in the distal region of the second diagonal. The two electrodes 19 are positioned such that they sample the activity at points 102 and 104. An arrhythmia is then induced by applying electrical pulses using an endocardial pacing lead. While the arrhythmia is sustained measurements are made. The wire 10 is then repositioned into the branch 106 of the second diagonal so that the two electrodes 19 are positioned at points 108 and 110, and the procedure is repeated. This is similarly done for points 112 and 114. The wire is then repositioned into the first diagonal branch 100 and the sequence of measurements repeated for points 116 and 118, 120 and 122, and 124 and 126. By comparing the timings of the electrical impulses from all the measurements with reference to a surface electrode, the location of the arrhythmia can be determined by selecting the sample point with the earliest occurrence.

A general premise for the search procedure is to locate the earliest occurring signal. A modification to the mapping procedure just described could be to interrogate the arteries, always repositioning the device toward the earlier occurring signal. With a two-electrode device as described, the signals from the two electrodes 19 are compared and if the signal from the proximal electrode is earlier, the wire 10 is retracted for the next reading; if the distal signal is earlier, the wire 10 is advanced.

Assuming the location of the arrhythmia is determined to be in the region of sample points 108 and 110, this can be confirmed by injecting a dose of iced saline into the vessel at that location. A small catheter is slid down over the guide wire 10 such that the distal tip of the catheter is beyond the bifurcation 128 and just proximal to sample point 110. While monitoring the activity distal to the catheter, and while the arrhythmia is present, cold saline is injected. The cold saline will temporarily stun the heart tissue locally and if that tissue is the site of the arrhythmia, the arrhythmia will cease. Embolization can then proceed.

Embolization (i.e., clogging) of the target artery will cause infarction of the ischemic tissue, thus permanently eliminating the arrhythmia. For the present example, the wire 10 is positioned in the branch 106 of the second diagonal so that the distal electrode is approximately at sample point 110. The electrode is then energized with sufficient RF energy to cause heating and coagulation of the blood at and near the electrode site. The coagulation will embolize the artery distal to the electrode. Embolization can be confirmed by injecting a small amount of contrast medium.

Just as the heart has its electrical activity which can be demonstrated on electrocardiograms, the brain also has its own electrical activity which can be demonstrated on electroencephalograms. It will thus be appreciated that the device of the present invention can be used in the cerebral vasculature to map the brain's electrical activity, just as it can in the coronary arteries to map the heart's activity.

It will also be appreciated by those skilled in the art that the size and steerability of the wire 10 make it ideally suited for the purpose of insertion into even very small veins and arteries.

As mentioned above, the wire 10 may be used in conjunction with a catheter tube which is slid over the wire 10 once the appropriate site has been located. Apart from saline, other flowable material may also be fed down the tube to cause, for example cell destruction. Similarly the tube may serve to drain flowable material from the site. In this context, the term flowable material includes not only fluids but also small solid particles dimensioned to pass along the tube e.g. tissue particles which have been removed from the parent tissue, or particles of degenerated material intima.

It will further be appreciated that the wire 10 may equally well be used in conjunction with a dilatation balloon or other interventional catheter to treat appropriate problem areas in the same setting as for the mapping and/or ablation procedures.

The invention claimed is:

1. A guide wire assembly including a central core having a proximal end and a distal end; a tubular body having a proximal end and a distal end, and comprising a plurality of helical spring sections surrounding at least a portion of the core; at least one electrode secured to the body and electrically insulated from the body, at least one of the at least one electrode being secured between two of the helical spring sections, and an electrical conductor connected to each electrode and extending within the tubular body.

2. A guide wire assembly of claim 1 having lateral dimensions from 0.010" to 0.038".

3. A guide wire assembly of claim 1, wherein the at least one electrode secured to the body is a unipolar electrode.

4. A guide wire assembly of claim 1, which includes a velocity sensing means connected to the body for sensing the velocity of blood flow in a blood vessel.

5. A guide wire assembly of claim 4, wherein the velocity sensing means includes a Doppler ultrasound transducer.

6. A guide wire assembly of claim 1, which includes a temperature sensor connected to one of the spring sections.

7. A guide wire assembly of claim 1, which includes a catheter tube means, passable over the cetral core and the tubular body, to define a pathway for passing flowable material along the pathway.

8. A guide wire assembly of claim 1, wherein the body includes a smooth proximal sleeve section.

9. A guide wire assembly of claim 1, wherein the core constitutes one of the electrical conductors.

10. A guide wire assembly of claim 1, wherein at least one electrode of the at least one electrode is supported on an electrode support, and wherein said at least one electrode supported on its electrode support is a tubular electrode supported on a cylindrical, electrically non-conductive tubular support with helical portions extending axially from both ends of the tubular support wherein the helical portions secure the tubular support to the body.

11. A guide wire assembly of claim 10, wherein the tubular support is formed in two parts which are axially connected to each other by means of complimentary locking formations formed at opposed ends of the two parts.

12. A guide wire assembly of claim 10, wherein the helical portions comprise helical grooves in an outer surface of the tubular support.

13. A guide wire assembly of claim 10, wherein each tubular electrode includes a conductive layer formed on part of an outer surface of its tubular support.

14. A guide wire assembly of claim 13, wherein the conductive layer comprises a conductive tube which is split longitudinally.

15. A guide wire assembly of claim 13, wherein the conductive layer comprises a conductive ribbon wound on the tubular support.

16. A guide wire assembly of claim 1, wherein at least one electrode is a tubular electrode including a central, electrically conductive cylinder having a first and a second end, and wherein electrically non-conductive helical portions extend axially from both ends of the cylinder.

17. A guide wire assembly of claim 1, wherein lateral dimensions of the core decrease towards the distal end of the core.

18. A guide wire assembly of claim 17, wherein the decrease in the lateral dimension s of the core comprises a plurality of discrete steps.

19. A guide wire assembly of claim 17, wherein the decrease in the lateral dimensions of the core comprises a continuous gradual taper.

20. A guide wire assembly of claim 17, wherein the distal end of the core is flattened from a point between 1 cm and 1.5 cm from the distal end to define an oval cross section.

21. A guide wire assembly of claim 1, wherein the guide wire includes a plurality of electrodes, and a helical spring section between each pair of electrodes.

22. A guide wire assembly of claim 1, wherein the distal end of the body is made of a radio-paque material.

23. A guide wire assembly of claim 1, wherein the helical spring sections include a distal spring section, and wherein at least the distal spring section of the plurality of helical spring sections is stretched towards the distal end of the body to provide greater flexibility towards the distal end of the body.

* * * * *